United States Patent
Krishnan et al.

(10) Patent No.: US 6,602,195 B1
(45) Date of Patent: Aug. 5, 2003

(54) MEDICAL ULTRASONIC IMAGING PULSE TRANSMISSION METHOD

(75) Inventors: Sriram Krishnan, San Jose, CA (US); Patrick J. Phillips, Sunnyvale, CA (US); Gregory L. Holley, Mountain View, CA (US); Ismayil M. Guracar, Redwood City, CA (US)

(73) Assignee: Acuson Corporation, Mountain View, CA (US)

( * ) Notice: Subject to any disclaimer, the term of this patent is extended or adjusted under 35 U.S.C. 154(b) by 94 days.

(21) Appl. No.: 09/767,158

(22) Filed: Jan. 22, 2001

Related U.S. Application Data

(63) Continuation-in-part of application No. 09/650,942, filed on Aug. 30, 2000, now abandoned.

(51) Int. Cl.$^7$ .................................................. A61B 8/00
(52) U.S. Cl. ..................................................... 600/447
(58) Field of Search ......................... 600/437, 440–447, 600/458; 73/625; 367/7, 11, 138; 128/916

(56) References Cited

U.S. PATENT DOCUMENTS

| | | | |
|---|---|---|---|
| 5,577,505 A | 11/1996 | Brock-Fisher et al. | |
| 5,632,277 A | 5/1997 | Chapman et al. | |
| 5,902,243 A | * 5/1999 | Holley et al. | 600/443 |
| 5,951,478 A | 9/1999 | Hwang et al. | |
| 6,221,018 B1 | * 4/2001 | Ramamurthy et al. | 600/443 |

OTHER PUBLICATIONS

Thomas et al., 09/514,803 "Contrast Pulse Sequences" (CPS), Feb. 29, 2000.

Bruno Haider and Richard Y. Chiao, "Higher Order Nonlinear Ultrasonic Imaging", 1999 IEEE Ultrasonics Symposium Proceedings.

* cited by examiner

*Primary Examiner*—Marvin M. Lateef
*Assistant Examiner*—Ali M. Imam

(57) ABSTRACT

A medical ultrasound imaging pulse transmission method transmits at least three pulses, including at least two pulses of different amplitude and at least two pulses of differing phase. The larger-amplitude pulse is transmitted with a larger aperture and the smaller-amplitude pulses are transmitted with respective smaller subapertures. The subapertures are arranged such that the sum of the subapertures used for the smaller-amplitude pulses is equal to the aperture used for the larger-amplitude pulse. In this way, pulses of differing amplitudes are obtained without varying the power level of individual transducer elements, and precise control over pulse amplitude is provided.

28 Claims, 9 Drawing Sheets

| Example | Pulse Sequence | Active Transducer Elements | |
|---|---|---|---|
| | | Positive Polarity Pulses | Negative Polarity Pulses |
| 1 | {1, −2, 1} | left half; right half | all |
| 2 | {1, −2, 1} | even; odd | all |
| 3 | {1, −2, 1} | 1-2, 5-6, 9-10, 13-14; 3-4, 7-8, 11-12, 15-16 | 1 - 16 |
| 4 | {1, −2, 1} | 1-4, 9-12; 5-8, 13-16 | 1 - 16 |
| 5 | {1, −2, 1} | 1-2, 13-16; 3-12 | 1 - 16 |
| 6 | {1, 1, 1, 1, −2, −2} | 1-32; 16-48; 33-64; 1-15, 49-64 | 1 - 64; 1 - 64 |
| 7 | {1, 1, 1, −3} | 1-21; 22-43; 44-64 | 1 - 64 |
| 8 | {1/2, 1/2, −1/3, −1/3, −1/3} | 1-32; 33-64 | 1 - 21; 22 -43; 44 - 64 |
| 9 | {1, i, 1, i, −2, −2i} | 0° : even; odd<br>90° : left half; right half | 180° : all<br>−90° : all |

FIG. 7

| Example | Transmit (Tx) Pulse Sequence | Receive weights | Tx event $x_1$ | Tx event $x_2$ | Tx event $x_3$ | Tx event $x_4$ | Tx event $x_5$ | Tx event $x_6$ |
|---|---|---|---|---|---|---|---|---|
| 10 | {i0.5 -1 -i0.5} | {-i 1 i} | even | full | odd | | | |
| 11 | {i0.5 -1 -i0.5} | {-i 1 i} | left half | full | right half | | | |
| 12 | {i0.5 -1 i0.5} | {-i -1 i} | even | full | odd | | | |
| 13 | {0.5 -1 1 -0.5} | {-2 -1 1 2} | even | full | full | odd | | |
| 14 | {1 -0.5 0.5 -1} | {1 2 -2 -1} | odd | full | full | odd | | |
| 15 | {i0.5 -1 1 -i0.5} | {i2 -1 1 -i2} | even | full | full | even | | |
| 16 | {0.5 -1 0.5 0.5 -1 0.5} | {1 1 1 1 1 1} | even | full | odd | even | full | odd |
| 17 | {-0.5 1 -0.5 0.5 -1 0.5} | {1 1 1 -1 -1 -1} | even | full | odd | odd | full | even |
| 18 | {-0.5 0.5 1 -1 -0.5 0.5} | {1 -1 1 -1 1 -1} | even | odd | full | full | odd | even |

FIG. 8

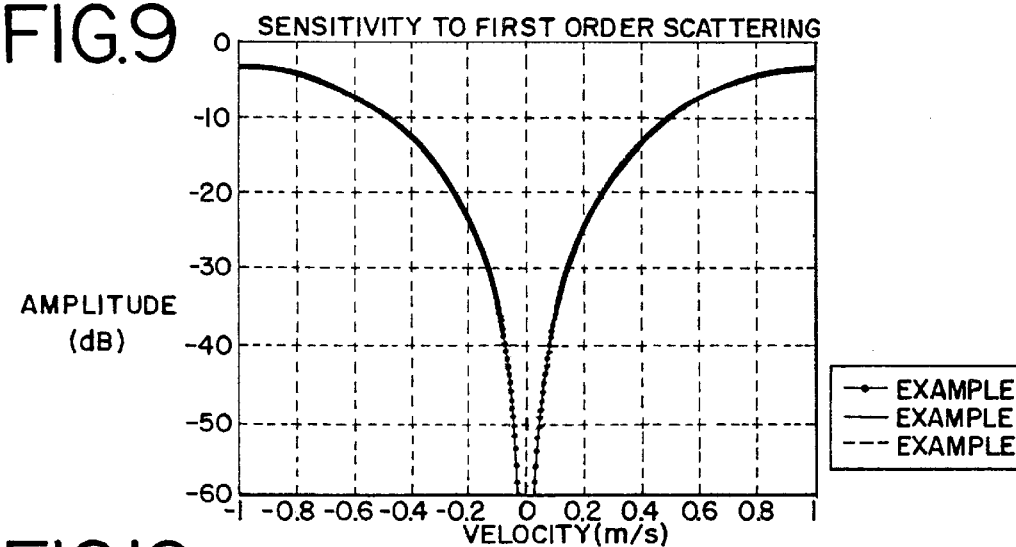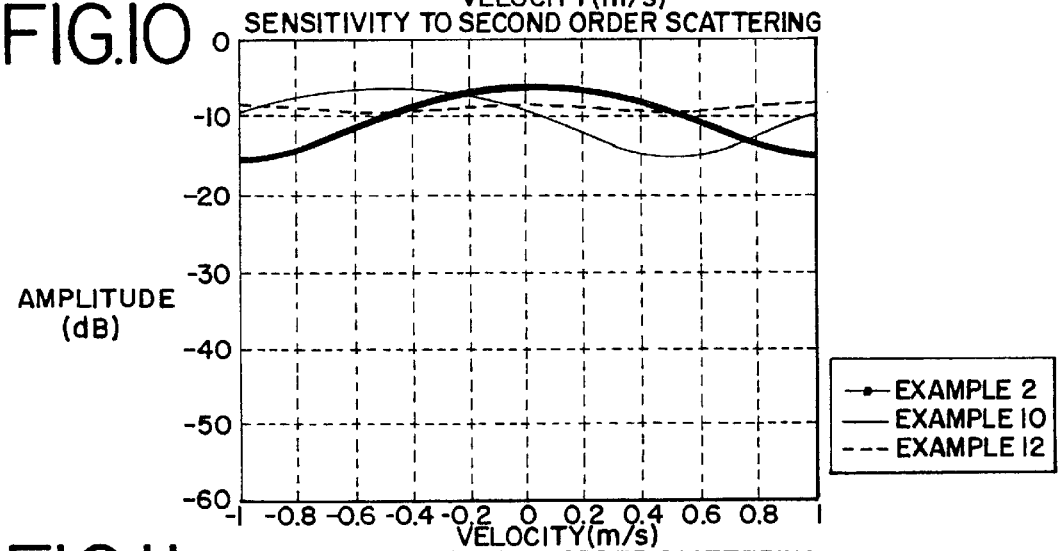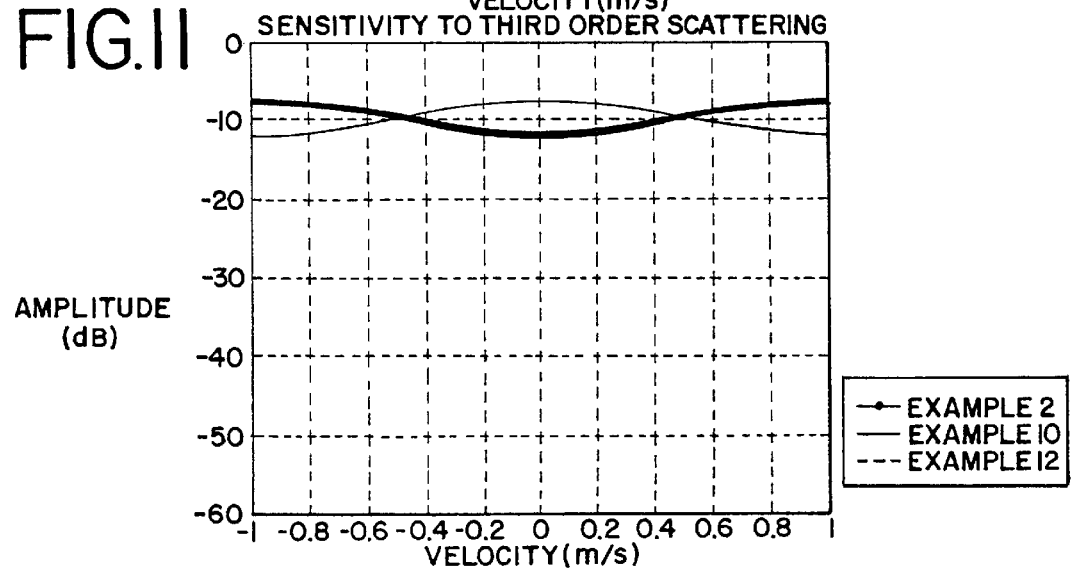

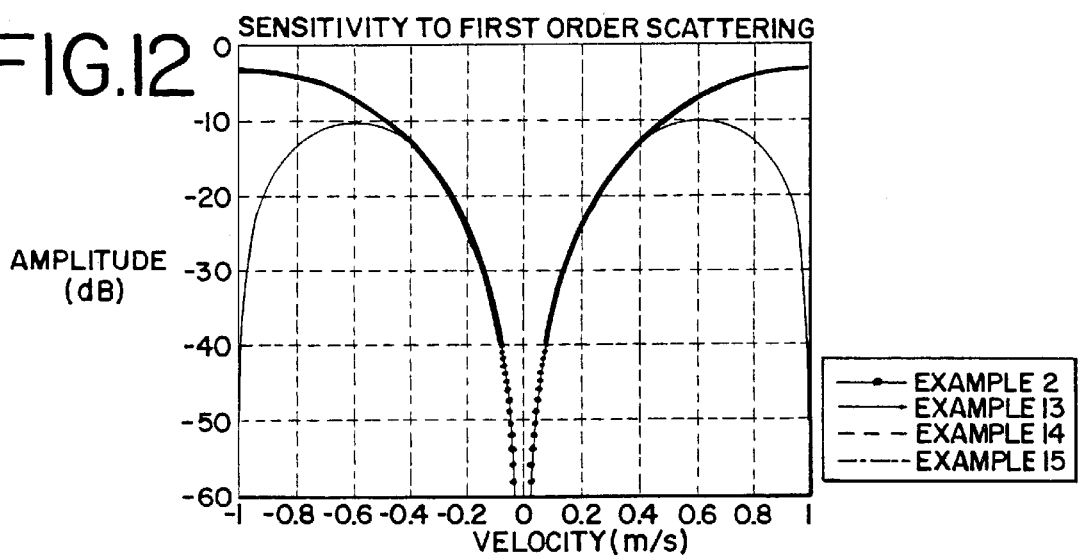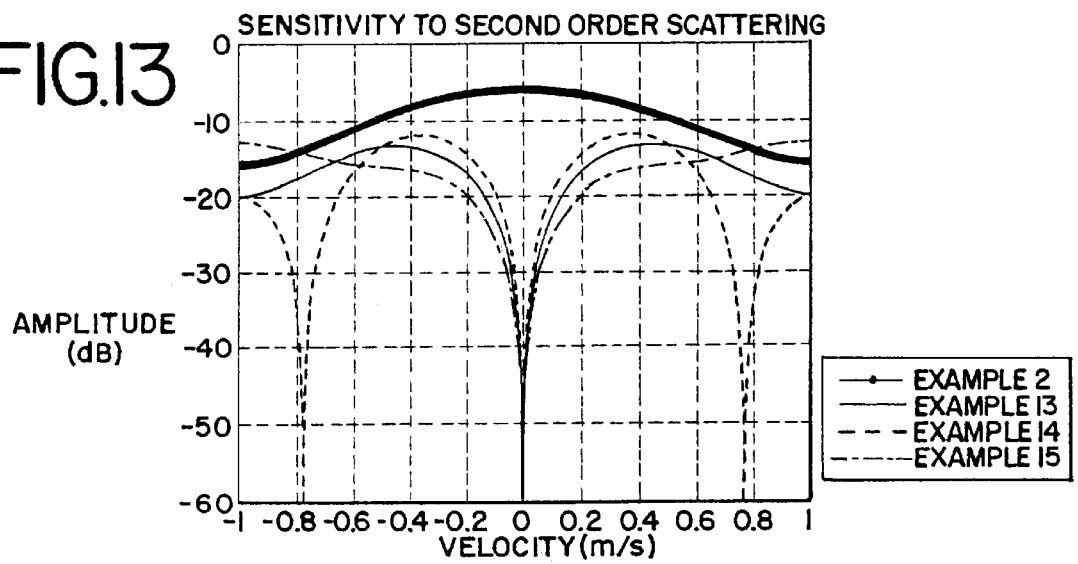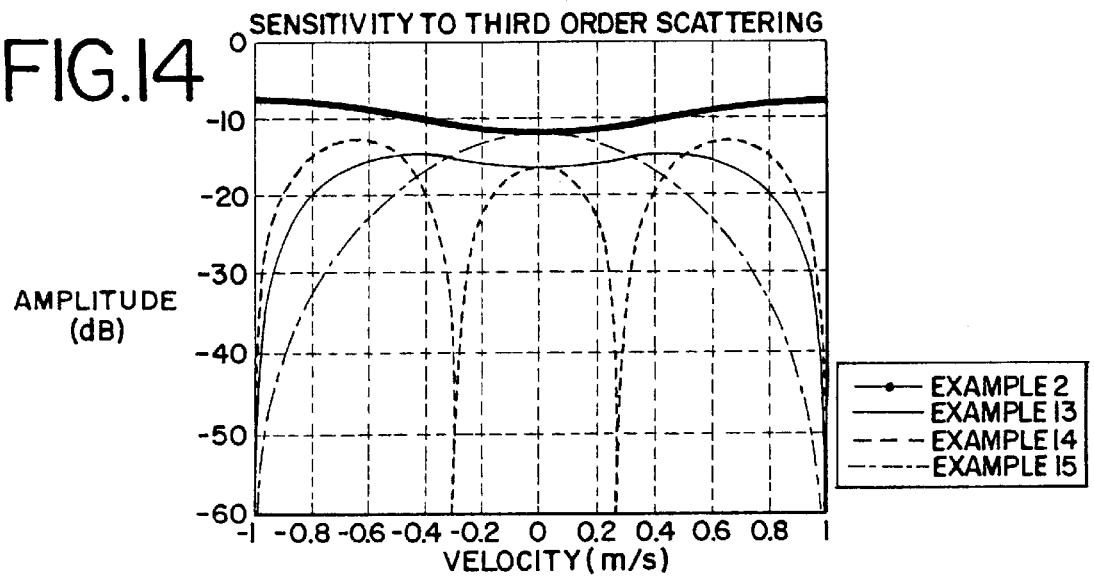

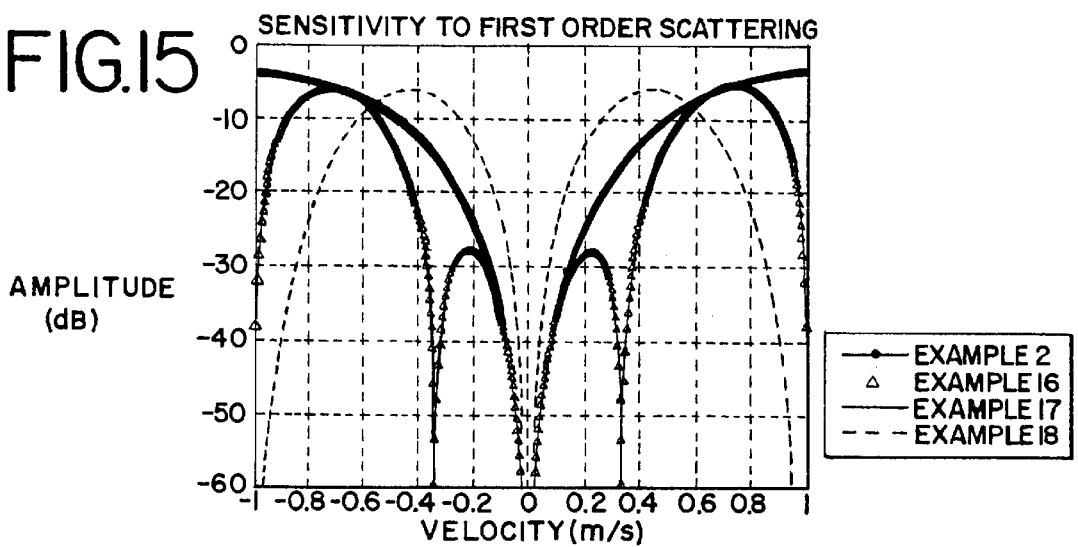
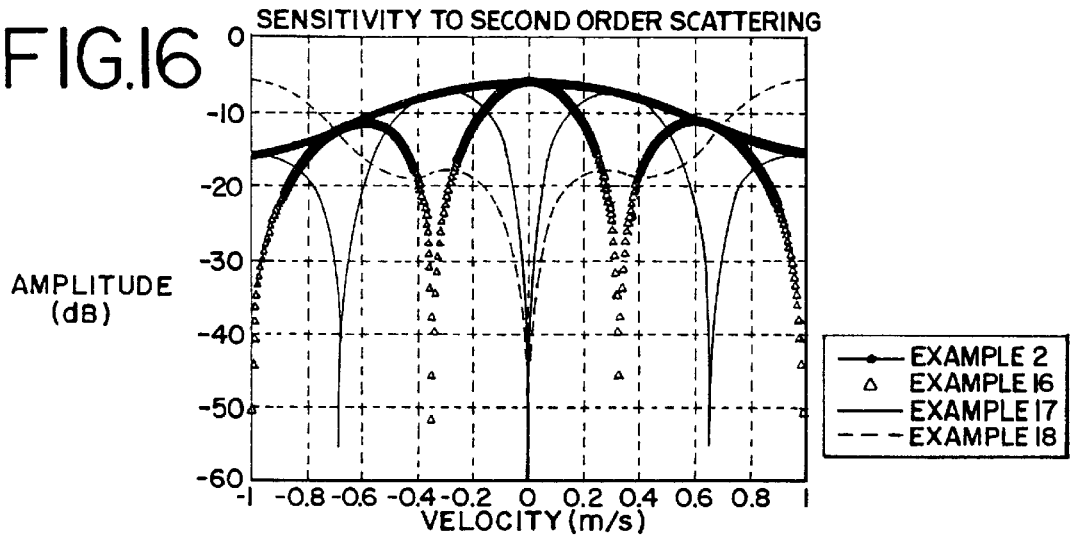
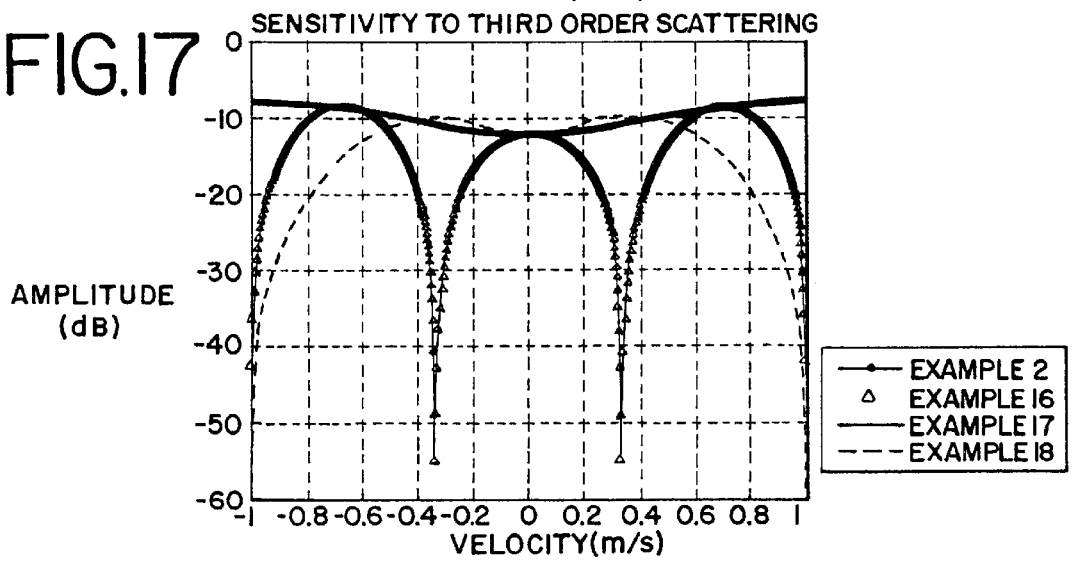

MEDICAL ULTRASONIC IMAGING PULSE TRANSMISSION METHOD

CROSS REFERENCE TO RELATED PATENT APPLICATION

This patent application is a continuation-in-part U.S. patent application Ser. No. 09/650,942 filed Aug. 30, 2000 abandoned, which is hereby incorporated by reference in its entirety.

BACKGROUND

This invention relates generally to medical ultrasonic imaging, and more specifically to improved methods for transmitting pulses with desired power levels.

Brock-Fisher et al. (U.S. Pat. No. 5,577,505) describe several methods for isolating non-linear responses from contrast agent and tissue. In one method, multiple pulses are fired along a line, where one pulse uses the entire transducer aperture. The aperture is then divided into two or more subapertures, and other pulses fired along the same line using the subapertures. The echo signals produced by these other pulses are then combined and subtracted from the echo signal produced by the first pulse to determine the non-linear response.

Thomas et al. (U.S. patent application Ser. No. 09/514,803) describe an alternative technique, called "Contrast Pulse Sequences," (CPS), where multiple pulses are transmitted into the body. These pulses have different transmit amplitudes and phases. For example, three pulses can be transmitted with amplitudes +1, −2, and +1. The three pulses are then summed on receive so that linear responses are cancelled, and non-linear responses are preserved.

In both approaches, different pulses with different amplitudes are used so that odd-order non-linearities are preserved. By contrast, pulse inversion techniques, such as described by Hwang et al. (U.S. Pat. No. 5,951,478) and Chapman et al. (U.S. Pat. No. 5,632,277), remove odd-order non-linearities because the amplitude of the transmit pulse does not change when the phase is inverted.

The technique described by Brock-Fisher et al. suffers from degraded sensitivity to second harmonic signals. Consider the case where three pulses are fired along an acoustic line. The first pulse is fired using the entire aperture; the second pulse is fired using the even elements of the aperture; and the third pulse is fired using the odd elements of the aperture. Assume that a target is located at the transmit focus of the aperture along the acoustic line. In this case, the amplitude from each of the two half-aperture firings will be about one half the amplitude of the full-aperture firing.

If the pressure at the target from the half-aperture firing is one half the amplitude of the full-aperture firing, and if we assume that the second harmonic response of the signal is proportional to the square of the pressure, then the second harmonic response from the half-aperture is one quarter that of the full-aperture firing. Since the half-apertures are fired twice and summed, the total second harmonic response from the half-apertures will be one half that of the full-aperture firing. In this technique, the sum of the responses from the half-apertures is then subtracted from the response from the full aperture, resulting in a second harmonic signal with an amplitude one half that of the full aperture firing by itself. Such a loss in signal may be unacceptable, especially since the non-linear signals may be weak to begin with.

This problem is overcome by the Contrast Pulse Sequences described by Thomas et al. In one example, three pulses are fired with amplitudes +½, −1, +½, and the resulting echo signals are summed on receive. Note the big difference between these sequences, and the sequences described by Brock-Fischer, is that the transmit phase changes with different firings. The second harmonic echo signals for these transmit pulses will be ¼, 1, and ¼, respectively. By summing these echo signals, the second-harmonic response will have an amplitude of 1.5. Note that the amplitude of the second harmonic signal is greater than the second harmonic response from any individual firing. Thus, the second harmonic signal is preserved while the fundamental signal is cancelled.

The CPS technique relies on the precise control of amplitude of the transmitted pulses. Non-linear elements of the transmitter circuitry and the transducer can make this quite difficult to achieve. For example, diodes in the transmitter circuitry may cause problems since they often result in a fixed voltage drop. Attempts to correct for these non-linearities can be quite difficult, since these non-linearities can vary with different transmit voltages.

BRIEF SUMMARY

One preferred embodiment described below addresses this problem by maintaining the same power level for each transducer element throughout a set of pulses that includes at least two pulses of different amplitude and at least two pulses of different phase. In this embodiment, the larger-amplitude pulse uses a larger aperture including a selected number of transducer elements. The smaller-amplitude pulses of different phase use smaller apertures, selected such that each of transducer elements that is active in the larger-amplitude pulse is active in one or the other (but not both) of the lower-amplitude pulses. In this way each transducer element is active for the same number of pulses at the same power level for both the larger-amplitude pulse or pulses and the smaller-amplitude pulse or pulses. This ensures that the echo signals from the pulse sequence, when summed, have the desired amplitudes to cancel the selected fundamental and/or harmonic frequencies.

Because the voltage applied to each transducer element is held constant when that transducer element is active, problems related to an ultrasound system's transmit non-linearities are to a large extent solved. All odd-order non-linearities are removed. Though even-order non-linearities of the transmitter or transducer will still exist, most ultrasound systems are designed to have very small even-order non-linearities on transmit. For example, non-linear voltage-to-pressure responses will not adversely affect pulse amplitude. Since the phase of the smaller-amplitude pulses is different from the phase of the larger-amplitude pulse, the response from second order non-linearities will be greatly improved over the technique described by Brock-Fisher.

This section has been provided by way of general introduction, and is not intended to limit the scope of the following claims.

BRIEF DESCRIPTION OF THE DRAWINGS

FIG. 7 is a table of alternative pulse transmission methods implemented with the imaging system of FIG. 1.

FIG. 8 is another table of alternative pulse transmission methods implemented with the imaging system of FIG. 1.

FIGS. 9, 10 and 11 are graphs of sensitivity to first, second, and third order scattering, respectively, versus velocity of contrast agent or similar non-linear scatterer for examples 2, 10, 12 and 12.

FIGS. 12, 13 and 14 are graphs of sensitivity to first, second, and third order scattering, respectively, versus velocity of contrast agent or similar non-linear scatterer for examples 2, 13, 14, and 15.

FIGS. 15, 16 and 17 are graphs of sensitivity to first, second, and third order scattering, respectively, versus velocity of contrast agent or similar non-linear scatterer for examples 2, 16, 17, and 18.

DETAILED DESCRIPTION OF THE PREFERRED EMBODIMENTS

Figure 1:
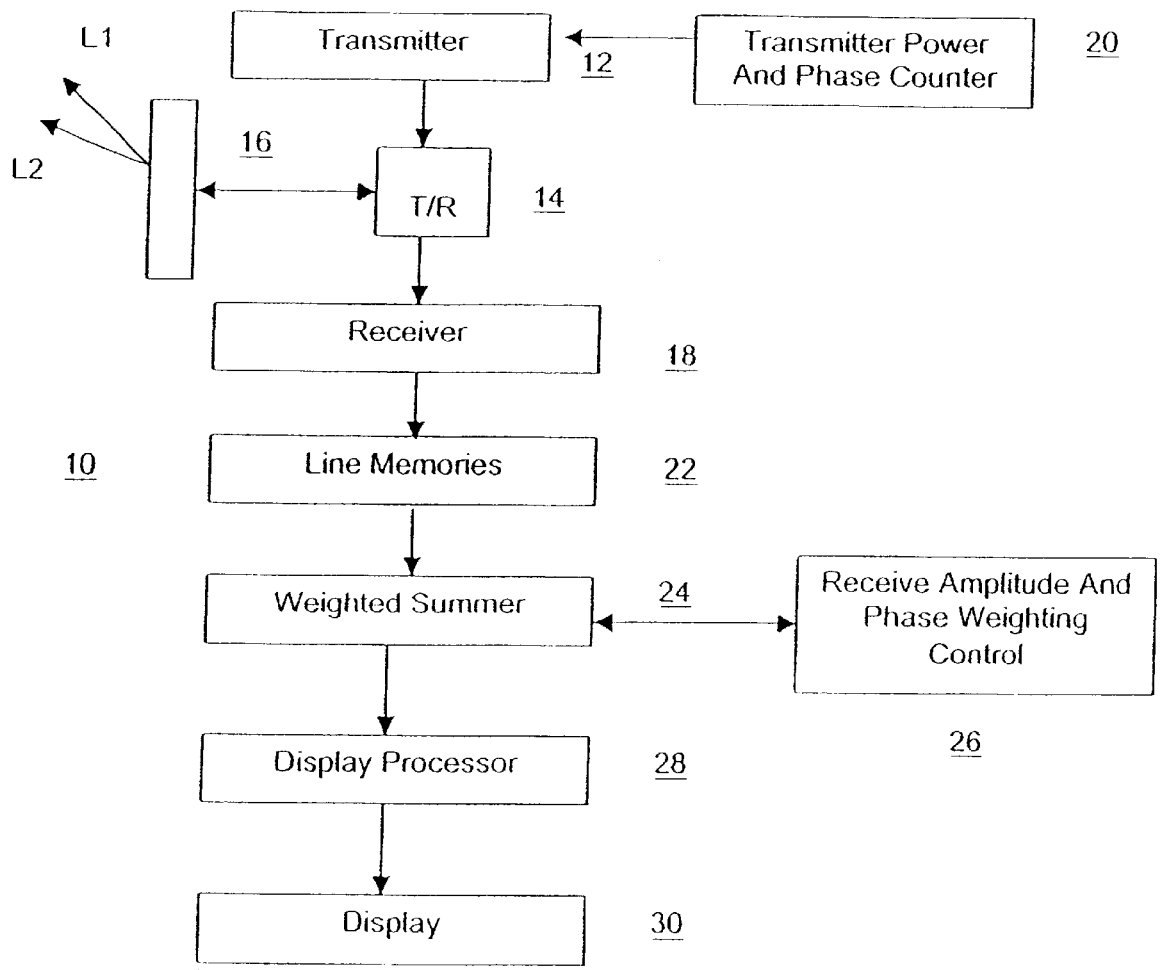
FIG. 1 is a block diagram of an ultrasonic imaging system used to practice the method of this invention.

FIG. 1 shows a block diagram of a medical diagnostic ultrasonic imaging system that can be used to implement the methods described below. The system 10 of FIG. 1 includes an ultrasonic transmitter 12 that is coupled to a transducer array 16 by a transmit/receive switch 14. The transmitter 12 applies transmit signals of selected waveform timing and phasing to the individual elements of the transducer array 16. In response, the transducer array 16 creates ultrasonic pressure waves, which conventionally are focused along one or more acoustic lines L1, L2. In the conventional manner, acoustic lines L1, L2 are steered across the region of interest by properly adjusting the phase and time delays of the transmit waveforms. Scatterers in the region of interest return ultrasonic energy to the transducer array 16, which in response forms echo signals that are applied by the transmit/receive switch 14 to a receiver 18. The receiver 18 applies appropriate phase and/or time delays to individual receive signals to cause the receive signals to add coherently from desired locations within the region of interest.

The transmitter 12, transducer array 16 and receiver 18 can take any desired forms. The widest variety of techniques can be used to implement the transmitter 12, including both analog and digital techniques. The following U.S. patents, all assigned to the assignee of the present invention, provide examples of the types and approaches that can be used to implement the transmitter 12: U.S. Pat. Nos. 4,550,607, 4,699,009, 5,148,810, 5,608,690, and 5,675,554. If desired, the transmitter 12 may be used to form unfocused or only slightly focused pressure waves in the region of interest. These examples are of course not intended to be limiting in any way.

Similarly, the transducer array 16 can take any desired form. The transducer array 16 can be a 1–, 1.25–, 1.5–, 1.75– or 2-dimensional array. By way of example, the transducers described in any of the following U.S. patents (all assigned to the assignee of the present invention) can readily be adapted for use with this invention: U.S. Pat. Nos. 5,261,408, 5,297,533, 5,410,208, 5,415,175, 5,438,998, 5,562,096, 5,657,295, 5,671,746, 5,706,820, 5,757,727, 5,792,058, 5,916,169, and 5,920,523. Once again, this list is not intended to be limiting, and any suitable transducer array can be used.

The receiver 14 can include beamformers implemented using any suitable technology. For example, the beamformers described in the following U.S. Patents (all assigned to the assignee of the present invention) can readily be adapted for use with this invention: U.S. Pat. Nos. 4,550,607, 4,699,009, and 5,555,534. Alternately, the receiver 14 can include one or more beamformers that form beams on a point-by-point basis rather than a scan-line basis. As before, these examples are not intended to be limiting.

Beamformed signals from the receiver 18 are stored in line memories 22. The line memories 22 can be formed as physically separate memories, or alternately they can be formed as selected locations in a common physical device. The beamformed signals associated with a given set of transmit pulses are stored in the line memories 22 and then weighted and summed in a weighted summer 24. The weighted summer 24 is controlled by a receive amplitude and phase weighting control 26 that provides the weighting values for both amplitude and phase that are used in the weighted summer 24. The weighted summer 24 forms a composite output signal by weighting the separate beamformed receive signals in any of the ways described below. The memories 22 and the summer 24 can be implemented using analog or digital techniques.

The composite output signal generated by the weighted summer 24 is applied to a display processor 28, which generates display signals that are applied to a display 30. For example, the composite output signals generated by the weighted summer 24 can be used to form conventional B-mode images on the display 30.

In the foregoing example, the composite output signal was formed from a weighted summation of receive signals that had been beamformed. The weighted summation can be performed at baseband, IF or RF. The weighted summation can in alternate embodiments be performed post-detection and even prior to beamforming. Similarly, the weighted summation can be performed either before or after scan conversion.

Figure 2:
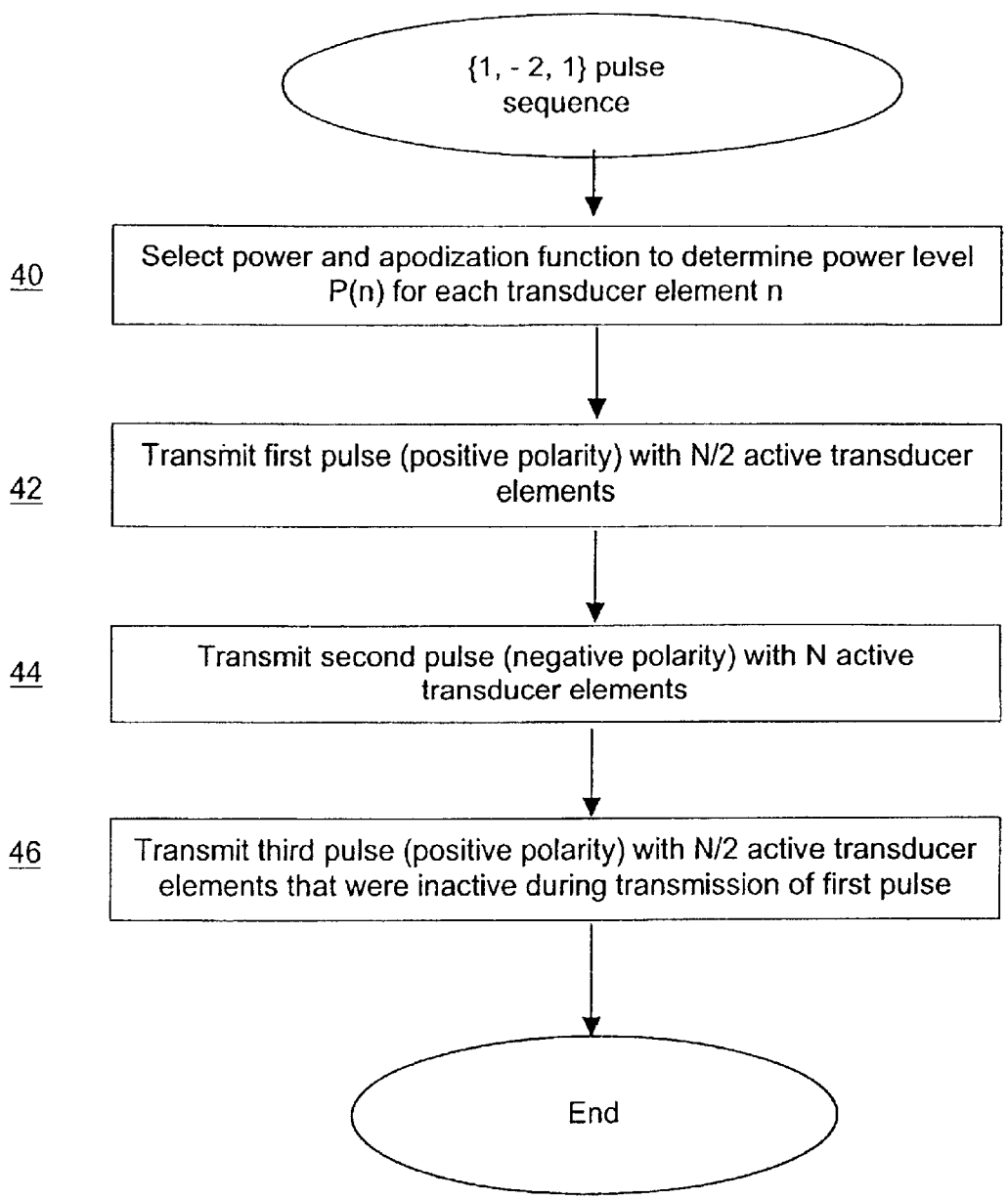
FIG. 2 is a flow chart of a pulse transmission method implemented with the imaging system of FIG. 1.
Figure 4:
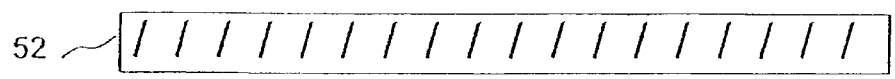

The imaging system 10 of FIG. 1 implements the transmission method of FIG. 2 and the receive method of FIG. 4. In the example of FIG. 2, a set of three ultrasonic pulses is transmitted along a given acoustic line characterized by a steering angle. This set of three pulses includes two subsets of pulses, each characterized by respective transmit phase. In this example the first and third pulses are of amplitude 1 and positive polarity (0 degree phase angle) and the second pulse is of amplitude 2 and negative polarity (180 degree phase angle).

As indicated in block 40, first the power and apodization are set to determine a power level P(n) for each transducer element n. This power level will be held constant throughout the set of three pulses, whenever the respective transducer element n is active. Any desired apodization function can be used.

Next, in block 42 a first pulse is transmitted with positive polarity, using only a subset of the available transducer elements. The subset will be referred to as a first subaperture, and in this example the first subaperture includes N/2 active transducer elements, i.e. ½ of the available transducer elements of the transducer array.

Next, in block 44 a second pulse is transmitted with negative polarity (i.e. a 180 degree phase shift with respect to the first pulse), using the full aperture of N active transducer elements. Note that since the power levels P(n) of each transducer element are maintained constant, and twice as many transducer elements are active for the second pulse as for the first pulse, the second pulse has twice the transmitted power of the first pulse.

Next, in block 46 a third pulse is transmitted with positive polarity, using N/2 active transducer elements. The active transducer elements for the third pulse are transducer elements that were inactive during transmission of the first pulse.

Figure 3:
FIGS. 3, 4 and 5 are exemplary diagrams illustrating active transducer element apertures in the first, second and third pulses of FIG. 2, respectively.
Figure 5:
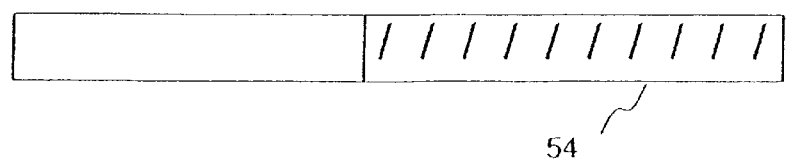

FIGS. 3, 4 and 5 schematically illustrate the apertures used for the first, second and third pulses, respectively. In FIG. 3, the subaperture 50 for the first pulse corresponds to the left half of the transducer array. The full aperture 52 used for the second pulse is shown as the lined region of FIG. 4. The second subaperture 54 used for the third pulse includes all of the transducer elements that are not included in the first subaperture 50.

Note that in this example each transducer element n is fired exactly once during the subset of pulses that are of positive polarity (i.e. the first and third pulses) and exactly once in the subset of pulses that are of negative polarity (i.e. the second pulse). Since the power level was maintained constant for each transducer during all three pulses whenever the transducer was active, the sum of the first and third pulses is substantially equal in amplitude to the second pulse.

Figure 6:
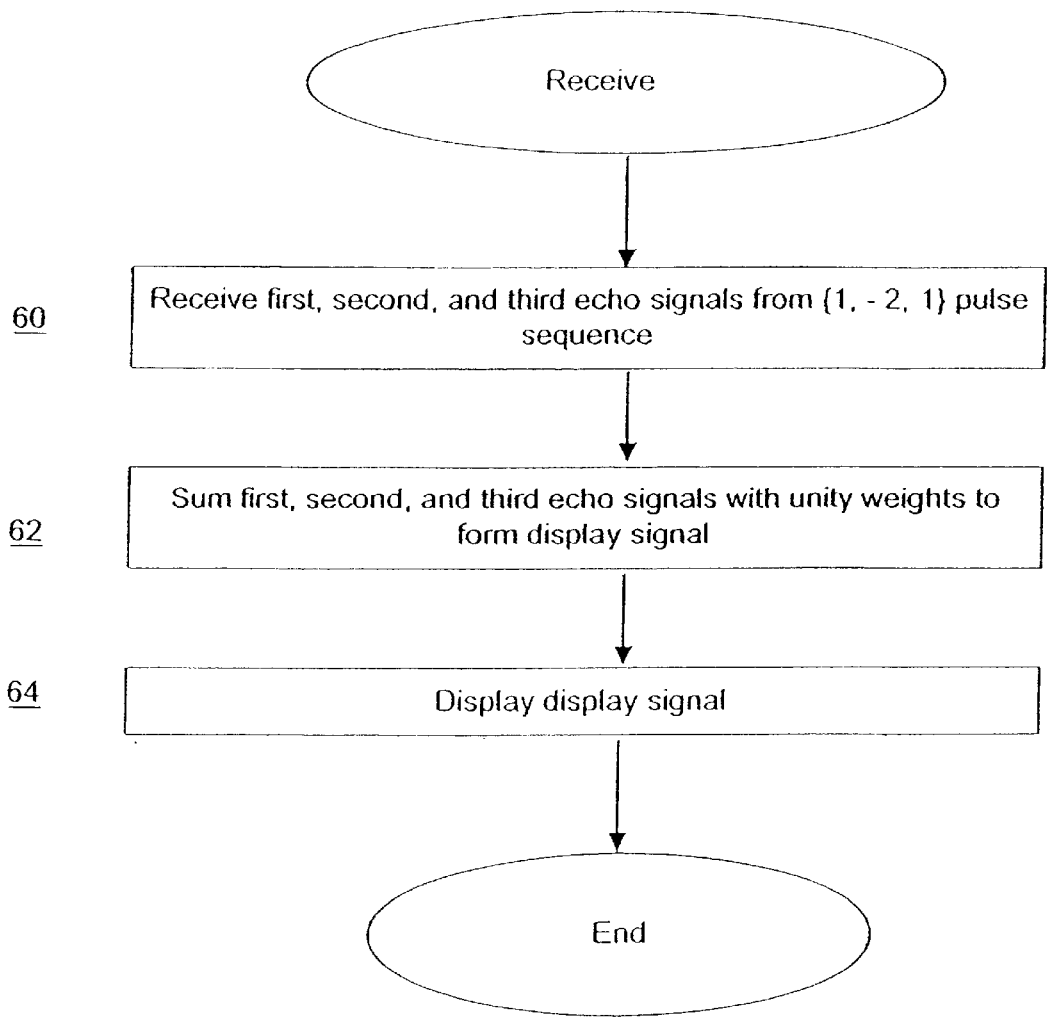
FIG. 6 is a flow chart of a receive method implemented with the imaging system of FIG. 1.

FIG. 6 shows a flow chart of a receive method used in conjunction with the pulse sequence of FIG. 2. In block 60, first, second and third echo signals are received in response to the first, second and third pulses of FIG. 2, respectively. In block 62, the first, second and third echo signals are coherently summed using unity-summing weights to form a display signal. In block 64, the display signal is processed for display on a monitor. As explained below, the fundamental components of the display signal are cancelled while higher order harmonic components of the display signal are preserved.

The techniques described above can be applied to a wide variety of pulse sequences that include pulses of different phase and amplitude. FIG. 7 provides a number of examples, numbered 1 through 9.

Example 1 of FIG. 7 was described above in conjunction with FIGS. 2–5.

Example 2 of FIG. 7 is closely related to Example 1, but in this case the first subaperture for the first positive-polarity pulse includes all even-numbered transducer elements, and the second subaperture for the second positive-polarity pulse includes all odd-numbered transducer elements.

Examples 3, 4 and 5 relate to a transducer array having 16 transducer elements. As shown in Example 3, transducer elements are grouped in pairs, with adjacent pairs of transducer elements active in either the first or second subaperture for the positive-polarity pulses, and all of the transducer elements active for the negative-polarity pulse.

Example 4 is similar to Example 3, except that the transducer elements are grouped into groups of four, with each group of four transducer elements active in one or the other of the first and second subapertures.

It is not essential that the same number of transducer elements be included in the first and second subapertures. For example, in Example 5 the first subaperture for the first positive-polarity pulse includes six transducer elements (1, 2, 13–16), while the second subaperture for the second positive-polarity pulse includes 10 transducer elements (3–12). In general, any desired subset of transducer elements can be used for the first subaperture, and the remaining subset of elements can be used for the second subaperture. Whether or not the two subapertures are equal, it is preferred that the two subapertures when added together equal the full aperture. The disadvantage of making the two subapertures unequal in size is that this will reduce the sensitivity of the approach to cubic fundamental signals.

The methods described above can be used with pulse sequences of varying lengths, and pulse sequences of four, five, six or more pulses can be used. For example, Example 6 of FIG. 7 shows a 6-pulse sequence including four positive-polarity pulses of amplitude 1 and two negative-polarity pulses of amplitude −2. This example uses a 64-element transducer array, and all 64 transducer elements are active for each of the negative-polarity pulses. Similarly, each of the transducer elements is active for only two positive-polarity pulses. In this example, the subapertures that are used include a left subaperture, a right subaperture, a central subaperture, and a peripheral subaperture. The subapertures do not have to be the same size, for the reasons discussed above.

Example 7 of FIG. 7 uses a 4-pulse sequence in which three positive-polarity pulses are of amplitude 1 and a single negative-polarity pulse is of amplitude −3. In this example, the full aperture is active for the negative-polarity pulse and three subapertures, each corresponding to one third of the full aperture, are active for the three positive-polarity pulses, respectively. In this case, the three subapertures when summed are equal to the full aperture. Again, the subapertures do not have to be equal to one another in the number of transducer elements, as long as the sum of the subapertures is equal to the full aperture. This technique can be extended to any desired length by breaking up the full aperture into N subapertures, and then firing N transmit pulses, each with a respective one of the subapertures.

Example 8 of FIG. 7 relates to a 5-pulse sequence in which the full aperture is never fired. In this example two pulses are fired with one-half amplitude and positive polarity and three pulses are fired with one-third amplitude and negative polarity. Note that each of the transducer elements 1 through 64 is fired once in the subset of positive-polarity pulses and once in the subset of negative-polarity pulses.

In the foregoing examples the pulse sequences have included pulses of positive and negative polarity. Other polarities are possible, including for example the pulse sequence of Example 9 of FIG. 7. In this example the pulse sequence includes pulses of four different phases: 0 degrees, 90 degrees (indicated by the symbol i), 180 degrees, and −90 degrees (indicated by the symbol −i). The subapertures used for the two 0 degree pulses correspond to even and odd subapertures, respectively, and the subapertures used for the two 90 degree pulses correspond to left and right subapertures, respectively. The full aperture is used for the pulses of 180 degrees and −90 degrees.

FIG. 8 provides examples of nine additional pulse sequences that can be used, showing the transmit pulse sequence and the receive weights in each case. FIG. 8 also provides examples of suitable sub-apertures for each transmit pulse.

Many different sub-apertures configurations may be used. Thus, Example 10 uses a sub-aperture of even transducer elements for the first pulse, odd transducer elements for the third pulse, and all (even plus odd) transducer elements for the second pulse. Example 11 is similar, but the sub-apertures for the first and third pulses have been chosen differently (left half and right half in this example).

Multiple element groups, or subgroups, may be defined and labelled as odd and even sub-apertures. Thus, odd, or even, sub-apertures can include alternating subgroups. For example, a preferred subaperture configuration is one where elements 0, 1, 2, 3, 8, 9, 10, and 11 define an odd subaperture in a 16-element transducer. Here, there are two subgroups composed of (0, 1, 2, 3) and (8, 9, 10, 11). The even sub-aperture would consist of two subgroups (4, 5, 6, 7) and (12, 13, 14, 15). Grouping elements into subgroups can minimize undesireable nonlinearities that may be present between firings that utilize different numbers of active elements.

In general, many variations are possible on the examples of FIG. 8. In particular, the order of transmit events within any given sequence can be modified as desired, and any suitable choice of sub-apertures can be used, including the sub-aperture choices of Examples 1–10.

FIGS. 9, 10, and 11 illustrate the sensitivity versus movement of contrast agent or similar nonlinear scatterer. (For all the graphs of sensitivity versus scatterer movement, the assumed ultrasound pulse center frequency is 3.85 MHz, the assumed pulse repetition interval is 200 microseconds, and the assumed velocity of sound is 1.54 millimeters per microsecond.) In these graphs the sensitivity for a stationary scatterer is indicated by the value(s) at a velocity of zero. Each graph in each figure has been normalized based on the incoherent noise power of the particular example sequence. FIG. 9 illustrates the sensitivity to first order scattering; FIG. 10 illustrates the sensitivity to second order scattering; and FIG. 11 illustrates the sensitivity to third order scattering. Note that in FIG. 11 the graphs for sequences 10 and 12 are identical. Example sequences 10 and 12 are more sensitive and therefore more specific to contrast agents than example 2 over the velocity range of −0.5 to 0.5 m/s due to greater sensitivity to third order scattering over this particular velocity range. This is particularly attractive for agent that is not moving or slowly moving such as agent accumulating in the myocardium, liver, or kidney.

FIGS. 12, 13, and 14 illustrate the sensitivity to first, second, and third order scattering, respectively, for example sequences 2, 13, 14, and 15. Note in FIG. 12 the graphs of example sequences 13, 14, and 15 are identical. Example sequences 13, 14, and 15 offer improved suppression of fundamental, or first order, scattering for greater velocities and significant suppression of second order scattering for low velocities, or no motion, compared to example sequence 2. Despite the reduced sensitivity to third order scattering for example sequences 13 and 14 with respect to example sequences 2 and 15 for low velocities, or no motion, example sequences 13 and 14 as well as example sequence 15 may be preferred for increasing contrast agent specificity. Example sequence 14 may be preferred over example sequence 13 since the transmit events that utilize subapertures are not interleaved by transmit events that utilize a full aperture. Since a subaperture configuration may produce an acoustic beam pattern that is less desirable than a full aperture, minimizing the time between any transmit events that utilize subapertures can be advantageous. Since motion between any two transmit events can degrade the combination of the two subapertures from being substantially identical to a full aperture transmit event, firing two subapertures during transmit events 2 and 3 (among transmit events 1, 2, 3, and 4) in example sequence 14, may be preferred over firing two subapertures during transmit events 1 and 4 in example sequence 13. The trade-off though is potential reduced sensitivity to third order scattering with example sequence 14. The combination of the potential image artifacts, sensitivity, and agent specificity will determine the preferred sequence. Clinical imaging and particular contrast agents should also be considered when choosing a particular sequence.

Notice, as shown here with examples 13 and 14, that rearranging the order of a particular sequence offers trade-offs between motion suppression and sensitivity for particular signal orders.

FIGS. 15, 16, and 17 illustrate the sensitivity to first, second, and third order scattering, respectively, for example sequences 2, 16, 17, and 18. Note in FIGS. 15 and 17 the graphs of example sequences 16 and 17 are identical. Example sequences 16, 17, and 18 offer further trade-offs for preferred imaging. These particular sequences sacrifice frame rate, due to six transmit events compared to three or four. However, example sequences 16 and 17 offer improved suppression of first order scattering and example sequence 18 offers improved suppression of second order scattering. For particular contrast agents and clinical applications these sequences may improve contrast agent specificity.

It should be apparent from the foregoing examples that each of the transducer elements n is active for a total of A(n) pulses within each subset of pulses having a given phase angle.

When splitting a full aperture into smaller subapertures on transmit, it is preferred, though not required, to distribute the number of active elements in the subaperture across the extent of the full aperture and not to group the active elements together on only one end of the full aperture. By evenly distributing the active elements in a subaperture across the array, desired suppression and retention of specific harmonic orders is maintained over a large area in the image. In contrast, splitting an aperture into two halves to form two subapertures, one on the left and one on the right, will produce less than optimal performance near the transducer. If a [1–2 1]×[1 1 1] contrast pulse sequence is used and the first transmitted pulse is formed from the left half of the full array and the third transmitted pulse is formed from the right half of the array, an interrogated area immediately in front of the left half of the array will not see substantial energy from the third transmit subaperture. In this case fundamental signals scattered from a stationary or near-stationary target could be adequately suppressed, but the three-pulse combination would not adequately detect third order scattering. Farther away from the transducer face and near the transmit focus better detection of third order scattering will be obtained. The preferred method is to distribute the active transmit elements across the array such that a target near the face of the transducer sees some transmitted energy from each of the firings.

An additional criterion that may be used to improve performance is to select a sequence that cancels all transmitted odd order nonlinearities. This will be explained by way of an example. Consider the two contrast pulse sequences $$[0.5-1\ 1\ 0.5]\times[-2-1\ 1\ 2]\qquad\text{sequence 1}$$

and $$[0.5-1-i\ i0.5]\times[2\ 1\ 1\ 2],\qquad\text{sequence 2}$$

where the transmitted half amplitudes are realized by the use of subapertures.

Also, consider one element E in an array that is active during the first three transmit pulses, but inactive during the last transmit pulse for both sequences. If the actual pressure amplitude present at the face of the transducer is P, the third order nonlinearities transmitted for the three active pulses for element E while the sequence 1 is used would be $P^3$, $-P^3$, and $P^3$, respectively. The combination with receive weights would produce $$-2P^3+P^3+P^3=0$$

maintaining perfect rejection of transmitted third order nonlinearities. For sequence 2 the same element E would produce pressure levels of $P^3$, $-P^3$, and $iP^3$, respectively.

This combination with the receive weights for sequence 2 would produce $$2P^3 - P^3 + iP^3$$

which is not equal to zero, leaving some transmitted third order nonlinearities still present in the processed signals. Thus, some sequences may be preferred if the amplitudes and phases of the multiple pulses are chosen to cancel transmitted odd order nonlinearities. The odd order nonlinearities may be any odd order inclusive of 1st (fundamental), 3rd, and 5th. Sequence 1 may be preferred over sequence 2 if third order-transmitted nonlinearities create suboptimal contrast agent specificity.

The selective aperture approaches described above are well suited for all of the pulse sequences identified as contrast pulse sequences (CPS) in above-identified U.S. patent application Ser. No. 09/514,803, assigned to the assignee of the present invention and hereby incorporated by reference, and for other transmit pulse sequences not specifically described in this referenced application. The following section provides further information regarding contrast pulse sequences.

Contrast Pulse Sequences

The following discussion considers transmitted pulses of the form $p_k(t) = a_k a(t) \cos(\omega_0 t)$, where $a_k$ defines the amplitude and phase of the pulse, $a(t)$ defines the envelope of the transmitted signal, and $\cos(\omega_0 t)$ represents the carrier frequency. We assume that the response (ignoring propagation delays) of a contrast agent is given by:

$$s_k(t) = \alpha_1 p_k(t) + \alpha_2 p_k^2(t) + \alpha_3 p_k^3(t) + \alpha_4 p_k^4(t) + \ldots$$

For pulse inversion techniques, where $a_1 = 1$ and $a_2 = -1$, $$s_1(t) + s_2(t) = 2\alpha_2 a^2(t) \cos^2(\omega_0 t) + 2\alpha_4 a^4(t) \cos^4(\omega_0 t) + \ldots$$

The resulting signal has no odd order scattering. However, for a CPS sequence such as $\{1, -2, 1\}$, where $a_1 = a_3 = 0.5$, $a_2 = -1$, and the minus sign indicates a phase shaft of 180° relative to the first pulse of the sequence, the resulting signal is given by:

$$s_1(t) + s_2(t) + s_3(t) = -0.5\alpha_2 a^2(t) \cos^2(\omega_0 t) - 0.75\alpha_3 a^3(t) \cos^3(\omega_0 t) - 0.875\alpha_4 a^4(t) \cos^4(\omega_0 t) + \ldots$$

which contains both even and odd order scattering. Only by varying the amplitude between at least two of the transmitted signals can one detect third order nonlinearities while suppressing first order scattering.

Although the third harmonic signal may seem to be of primarily academic interest, much of the third harmonic signal appears at the in fundamental frequency. (Note the trigonometric identity $\cos^3(\omega_0 t) = 0.75\cos((\omega_0 t) + 0.25\cos(3\omega_0 t)$.) Therefore much of the third harmonic scattering appears at the fundamental frequency and can easily be detected.

Note that the third order scattering components (that appear at the fundamental frequency) cannot be detected by pulse sequences consisting of equal amplitude pulses with opposite (0 degree and 180 degree) phase. Only by varying the amplitude between at least two of the transmitted signals can one detect third order nonlinearities at the fundamental frequency while suppressing first-order scattering. (One can detect third order scattering at 3 times the fundamental frequency while suppressing the first-order scattering by transmitting pulses of constant amplitude if the phase between at least two of the transmitted pulses differs by an amount other than 0 degree or 180 degree.)

Using a six-pulse CPS, it is possible to suppress both the fundamental and second harmonic signals and image only third order and higher scattering, opening up the possibility of improving the specificity of contrast agent detection with nonlinear scattering. For this six-pulse CPS, the pulses can be described by:

$$p_1(t) = 0.5a(t)\cos(\omega_0 t)$$

$$p_2(t) = 0.5a(t)\sin(\omega_0 t)$$

$$p_3(t) = -a(t)\cos(\omega_0 t)$$

$$p_4(t) = -a(t)\sin(\omega_0 t)$$

$$p_5(t) = 0.5a(t)\cos(\omega_0 t)$$

$$p_6(t) = 0.5a(t)\sin(\omega_0 t)$$

This pulse sequence can be written as, $\{1, i, -2, -2i, 1, i\}$, where the minus sign represents a phase shift of 180° and i represents a phase shift of 90° relative to the first pulse of the sequence. After summing up the received signals (with uniform receive weighting) the result would be:

$$s_1(t) + s_2(t) + s_3(t) + s_4(t) + s5(t) + s_6(t) = -0.75\alpha_3 a^3(t)\cos^3(\omega_0 t) - 0.75\alpha_3 a^3(t)\sin^3(\omega_0 t) + 2.25\alpha_4 a^4(t)\cos^4(\omega_0 t) + \ldots$$

which contains only scattering from third order and higher terms. There are shorter pulse sequences such as $\{1, i, -2, -2i\}$ with receive weights $\{2, 2, 1, 1\}$ that can reject both the first and second order scattering. The six-pulse sequence was chosen because it is simple and also provides good immunity to motion artifacts generated from insufficient suppression of signals of undesired orders (such as first) from moving scatterers.

In addition to the advantage of rejecting specific orders of scattering, contrast pulse sequences can be designed to reduce artifacts due to motion. The CPS $\{1, -2, 1\}$ discussed above is more effective at rejecting first order scattering from moving targets than pulse inversion.

For third order scattering, the CPS $\{1, -2, 1\}$ has excellent sensitivity while pulse inversion has poor sensitivity to third order scattering. Both the CPS $\{1, -2, 1\}$ and the pulse inversion sequence have good sensitivity to second order scattering.

An alternative to imaging contrast agents via higher order nonlinear response is the loss of correlation (LOC) effect. The LOC effect relies on the first pulse altering the contrast agent in some way that is detected by the second pulse. The contrast pulse sequence $\{1, -2, 1\}$ has very good sensitivity to the LOC effect because the first pulse alters the contrast agent (usually by destroying, releasing encapsulated gas, modifying the characteristics of the agent shell, or moving the agent), so the response to the second pulse (for first order scattering) is not twice the amplitude and of the opposite phase as the response to the first pulse. Similarly, the response to the third pulse is not equal to the response to the first pulse, again because of the modification of the contrast agent. Therefore, when the responses are summed, the result is not zero. For tissue, which does not change between the insonifications, the resulting LOC signal is zero (neglecting motion). In the presence of tissue motion, the CPS $\{1, -2, 1\}$ has the same improved rejection of first order scattering over the pulse inversion sequence $\{1, -1\}$.

As the name implies, contrast pulse sequences are sequences of pulses that can be used for conventional B-mode imaging. Such pulses include:

unipolar binary pulses, bipolar binary pulses, pulses achieved by modulating a carrier frequency, as described in Hossack U.S. Pat. No. 5,608,690, binary pulses that are smoothed by the non-linear response of elements in the transmit path, and pulses generated by storing a waveform in memory and then presenting the contents of the memory (in sequence) to a digital-to-analog converter.

Although we prefer to use pulses with characteristics (center frequency, bandwidth, and shape) that are similar to those used for conventional B-mode imaging, no particular pulse shape is required for contrast pulse sequences. For this reason, any pulse shape or pulse generation technique can be used with this invention.

When characterizing a contrast pulse sequence we frequently use a notation such as {1, −2, 1}. This notation describes both the amplitude and phase of the transmitted pulses. We recognize that the actual transmitted amplitudes are normalized to the maximum allowable output, as determined by either system limitations (peak voltages available, maximum pulser power, etc.), regulatory limits on acoustic output (MI, ISPTA, TI, etc.), or the desire by the clinician to limit acoustic output to achieve a desired result during the ultrasound exam (limiting exposure of the patient, avoiding destruction of contrast agents, etc.). The notation also depicts the phase of the transmitted pulses, using a negative sign to indicate a 180 degree phase shift and the symbol i to indicate a 90 degree phase shift. (Phases are not limited to 0, 90, 180, and 270 degrees. Any arbitrary phase can be used for transmit or receive.) In Table 1 we present various characteristics of several contrast pulse sequences.

notation). The transmitted amplitude (relative to the peak desired output) for each of the pulses is listed in the second column. The third column provides the corresponding phase for each of the transmitted pulses. For pulses generated by modulating a carrier frequency, this phase is the phase of the carrier relative to the time at which transmission of the pulse begins. (For example, a carrier that is at its positive peak when transmission begins is a cosine wave and has zero phase in this embodiment, while a carrier that is at zero and has a positive slope when transmission begins is a sine wave and has a phase of 90 degrees in this embodiment.) Note, the use of the start of transmission as the time reference for determining phase is convenient, but arbitrary. Any time reference that is the same for all transmitted pulses can be used. For unipolar binary waveforms, this phasing of the CPS pulses is achieved by delaying the pulses as appropriate. A 90 degree phase corresponds to a delay of ¼ of the period of the center frequency of the pulse, and a 180 degree phase corresponds to a delay of one-half cycle at the center frequency of the pulse. For bipolar binary waveforms, a phase of 90 degrees is again achieved by delaying the pulse by ¼ of the period of the center frequency of the pulse, and a 180 degree phase can be achieved by inverting the pulse.

Upon reception of echoes resulting from each transmitted pulse, the received echoes are multiplied by receive weighting factors (which may vary in amplitude and phase for each transmitted pulse), and these weighted received signals are summed to produce the composite output signal. These receive weighting factors are chosen to suppress specific orders of scattering. For example, if only first order scattering is to be suppressed, then the sum of each transmit amplitude times the respective receive amplitude should equal zero.

TABLE 1

Exemplary Contrast Pulse Sequences

| CPS name | Transmitted Amplitude (fraction of maximum output) | Transmitted Phase | Receive Weighting Amplitude | Receive Weighting Phase | Sensitivity to $1^{st}$ order signal | Sensitivity to $2^{nd}$ order signal | Sensitivity to $3^{rd}$ order signal |
|---|---|---|---|---|---|---|---|
| {1, −2, 1} | ½, 1, ½ | 0, 180, 0 | 1, 1, 1 | 0, 0, 0 | 0 | 1.5 | ¾ |
| {1, i, −2, −2i, 1, i} | ½, ½, 1, 1, ½, ½ | 0, 90, 180, 270, 0, 90 | 1, 1, 1, 1, 1, 1 | 0, 0, 0, 0, 0, 0 | 0 | 0 | $\frac{3\sqrt{2}}{4}$ |
| {2, 1, −1, −2} | 1, ½, ½, 1 | 0, 0, 180, 180 | 3, 8, 24, 5 | 0, 0, 0, 180 | 0 | 6 | 6 |
| {1, i, −2, −2i} | ½, ½, 1, 1 | 0, 90, 180, 270 | 2, 2, 1, 1 | 0, 0, 0, 0 | 0 | 0 | $\frac{3\sqrt{2}}{4}$ |
| {1, −2, 1, −2, 1} | ½, 1, ½, 1, ½ | 0, 180, 0, 180, 0 | 1, 2, 6, 2, 1 | 0, 0, 0, 0, 0 | 0 | 6 | 3 |
| {1, −2, 2, −2, 1} | ½, 1, 1, 1, ½ | 0, 180, 0, 180, 0 | 1, 2, 6, 2, 1 | 0, 0, 0, 0, 0 | 0 | 7.5 | ¾ |
| {1, −2} | ½, 1 | 0, 180 | 2, 1 | 0, 0 | 0 | 1.5 | ¾ |
| {1, 2, 1} | ½, 1, ½ | 0, 0, 0 | 1, 1, 1 | 0, 180, 0 | 0 | 2 | 6 |
| {3, −5, 4, −5} | 0.6, 1, 0.8, 1 | 0, 180, 0, 180 | 5/3, 3, 3.75, 1 | 0, 0, 0, 0 | 0 | 7 | 1.72 |
| {2, −5, 3, −5} | 0.4, 1, 0.6, 1 | 0, 180, 0, 180 | 2.5, 3, 5, 1 | 0, 0, 0, 0 | 0 | 6.2 | 2.76 |

The conventional name (a sequence of numbers) for each contrast pulse sequence is listed in the first column. The number of pulses in each contrast pulse sequence is determined by the number of numerical entries in the name. For example, the first CPS {1, −2, 1} has three pulses, while the second CPS {1, i, −2, −2i, 1, i} has 6 pulses (note that 'i', the square root of negative 1, is considered a number in this A good method for representing the complex nature of both the transmit amplitude and the receive weights is to use complex notation, in which a pulse with a transmit amplitude of Y and a transmit phase of 180 degrees is represented by −½. Similarly, a pulse with a transmit amplitude of 2 and a transmit phase of 90 degrees is represented by 2i. This notation easily extends to other phase angles by combining real and imaginary values, for instance, a pulse with an amplitude of 2 and a phase of 45 degrees would be represented by ($\sqrt{2}+i\sqrt{2}$).

Looking at the first contrast pulse sequence of Table 1, the complex transmit amplitudes are ½, −1, and ½. The complex receive weights are all 1. Therefore, the sum of the complex transmit amplitudes times the complex receive weights is:

$$(\frac{1}{2} \times 1) + ((-1) \times 1(\frac{1}{2} \times 1) = \frac{1}{2} + (-1) + \frac{1}{2} 0.$$

Therefore, first order scattering will be suppressed in the composite output signal by this complex pulse sequence. The sensitivity to first order scattering for each contrast pulse sequence is listed in Table 1.

To determine the sensitivity of a contrast pulse sequence to second order scattering, the complex transmit pulse amplitudes are first squared, then multiplied by the corresponding complex receive weights and summed. Using the $\{1, -2, 1\}$ sequence again, we find that the second order sensitivity is given by:

$$((\frac{1}{2})^2 \times 1) + ((-1)^2 \times 1) + ((\frac{1}{2})^2 \times 1) = \frac{1}{4} + 1 + \frac{1}{4} \frac{3}{2}.$$

Similarly, the third order sensitivity is determined by squaring the complex transmit amplitudes then multiplying by the complex conjugate of the complex transmit amplitude before weighting with the complex receive amplitudes and summing. The $\{1, -2, 1\}$ CPS third order sensitivity is thus:

$$((\frac{1}{2})^3 \times 1) + ((-1)^3 \times 1) + ((\frac{1}{2})^{3 \times 1}) = \frac{1}{8} + (-1) + \frac{1}{8} = -\frac{3}{4}.$$

Since we are not interested in the phase of the sensitivity, the corresponding entry in the table does not include the negative sign in the result.

Turning to the second contrast pulse sequence $\{1, i, -2, -2i, 1, i\}$ of Table 1, we see that the sensitivity to both first and second order scattering is zero:

$$((\frac{1}{2} \times 1) + ((1i/2 \times 1) + ((-1) \times 1) + ((-1i) \times 1) + (\frac{1}{2} \times 1) + (1i/2 \times 1) = \frac{1}{2} + (-1) + \frac{1}{2} + 1i/2 + (-1i) + 1i/2 = 0;$$

$$((\frac{1}{2})^2 \times 1) + ((1i/2)^2 \times 1) + ((-1)^2 \times 1) + ((-1i)^2 \times 1) + ((\frac{1}{2})^2 \times 1) + ((1i/2)^2 \times 1) = \frac{1}{4} + -\frac{1}{4} + 1 + (-1) + \frac{1}{4} + -\frac{1}{4} = 0.$$

The third order sensitivity for this sequence is given by:

$$((\frac{1}{2})^3 \times 1) +$$

$$((1i/2)^3 \times 1) +$$

$$((-1)^3 \times 1) + ((-1i)^3 \times 1) +$$

$$((\frac{1}{2})^3 \times 1) + ((1i/2)^3 \times 1) =$$

$$\frac{1}{8} + -\frac{1}{8} + (-1) + (1i) +$$

$$\frac{1}{8} + -1i/8 = -$$

$$\frac{3}{4} + 3i/4.$$

In the table we have once again shown the magnitude of the sensitivity because we are not interested in the phase.

Evaluating the contrast pulse sequence $\{2, 1, -1, -2\}$ with non-unity receive weighting, we obtain the following sensitivities for first through third order scattering:

$(1 \times 3) + (\frac{1}{2} \times 8) + (-\frac{1}{2} \times 24) + ((-1) \times (-5)) = 3 + 4 + (-12) + 5 = 0;$    ($1^{st}$ order)

$(1^2 \times 3) + ((\frac{1}{2})^2 \times 8) + ((-\frac{1}{2})^2 \times 24) + ((-1)^2 \times (-5)) = 3 + 2 + 6 + (-5) = 6;$    ($2^{nd}$ order)

$(1^3 \times 3) + ((\frac{1}{2})^{3 \times 8}) + ((-\frac{1}{2})^3 \times 24) + ((-1)^3 \times (-5)) = 3 + 1 + (-3) + 5 = 6;$    ($3^{rd}$ order)

As the preceding analysis shows, the particular order in which the pulses are transmitted does not affect the rejection of specific orders of scattering for stationary scatterers. However, this order is important if motion is present. As shown previously, contrast pulse sequences can reject specific orders of scattering from moving scatterers better than previous techniques such as the pulse inversion technique. In addition, changing the order of pulses in the sequence will affect rejection of signals from moving scatterers.

Finally, a simple contrast pulse sequence $\{1, -2, 1\}$ can be extended to $\{1, -2, 1, -2, 1, \ldots\}$ to improve rejection of signals from moving scatterers. The improved motion rejection is gained by using more pulses (as improved rejection of clutter signals is improved with more pulses in flow imaging), but unlike the straightforward extension of pulse inversion (the sequence $\{1, -1, 1, -1, 1\}$) the contrast pulse sequence retains sensitivity to third order scattering.

The previous discussion has assumed that sequential transmissions of pulses in a contrast pulse sequence are steered in the same, or substantially the same, direction. This approach ensures that the same scatterers are insonified with each pulse and therefore that signals arising from sequential pulses differ only as a result of changes in the transmitted pulse. (Note that small changes in insonification direction can be made with this approach, such that changes in the received signals due to the change in insonification direction are similar in amplitude to the changes in the received signals due to noise, without degrading the performance of contrast pulse sequences.)

U.S. patent application Ser. No. 09/282,396, now U.S. Pat. No. 6,193,663, assigned to the assignee of the present invention, describes the Alternating Line Phase technique, whereby signals arising from transmission along two different lines can be processed to eliminate scattering of an undesirable order. In accordance with an embodiment of this invention, an application of Alternating Line Phase to CPS is to split one of the complex contrast pulse sequences into two sequences, and to transmit these two different sequences along two adjacent scan line directions. As an example, the $\{1, i, -2, -2i, 1, i\}$ CPS can be split into two sequences $\{1, -2, 1\}$ and The real sequence and the imaginary sequence are transmitted along adjacent scan lines, and the received signals from the adjacent lines (after receive weighting and summing) are summed. The individual lines reject first order scattering, and when the signals from adjacent transmit lines are added the second order scattering is rejected, just as with the original six pulse sequence. This technique can be extended to more lines and any number of pulses.

In accordance with another embodiment of the invention, it is possible to improve the signal to noise ratio (SNR) of CPS imaging while retaining image quality parameters (spatial resolution, clutter suppression, etc.) by using coding schemes to increase transmitted acoustic power without increasing peak transmitted acoustic amplitude.

Since CPS imaging transmits pulses of varying amplitudes, and the maximum amplitude is limited, pulses with lower amplitudes will result in signals with poorer SNR than those with the maximum amplitude. This can be corrected by using coding to lengthen the lower-amplitude pulses (without reducing axial resolution) until the amplitude (post pulse compression) of these pulses equals those of the maximum-amplitude pulses. A good candidate for this encoding is a chirp code, since chirp codes require only one pulse, and the shape of a chirped pulse can be easily predicted after nonlinear propagation or scattering. See the discussion in U.S. patent application Ser. No. 09/282,396, now U.S. Pat. No. 6,193,663, assigned to the assignee of the present invention. Using the example of a $\{1, -2\}$ CPS, if the smaller-amplitude pulse were lengthened to the point that its amplitude (post pulse compression) was the same as the larger pulse (in this case the complex receive weights would be $\{1, 1\}$), then the SNR (for all order scattering) would be increased by 4 dB. In general, it is preferred to use a longer code with lower peak amplitude pulses than with higher peak amplitude pulses.

Concluding Remarks

Of course, many alternatives are possible. For example, other pulses in addition to those described above may be transmitted, and in some pulse sequences selected transducer elements may be inactive for all pulses within the sequence. Thus, the term "aperture" is not intended to be restricted to the full aperture of the transducer array, and a sub-aperture may be referred to as an aperture. The term "set" and "subset" each refer to one or more elements.

The foregoing detailed description has discussed only a few of the many forms that this invention can take, and this description is therefore intended by way of illustration, not limitation. It is only the following claims, including all equivalents, that are intended to define the scope of this invention.

What is claimed is:

1. An ultrasonic pulse transmission method comprising:
   (a) transmitting with an ultrasonic imaging system a set of at least three ultrasonic pulses with a transducer array comprising N transducer elements, said set of pulses comprising at least two subsets of pulses, each subset characterized by a respective transmit phase, at least two of the transmit phases differing from one another;
   (b) each of the pulses of the set comprising a respective aperture, the apertures of at least two of the pulses differing in number of active transducer elements;
   (c) the apertures selected such that each transducer element n in the apertures is active for a total of A(n) pulses in each of the subsets.

2. An ultrasonic pulse transmission method comprising:
   (a) transmitting with an ultrasonic imaging system a set of at least three ultrasonic pulses with a transducer array comprising N transducer elements, said set of pulses comprising at least two subsets of pulses, each subset characterized by a respective transmit phase, at least two of the transmit phases differing from one another;
   (b) each of the pulses of the set comprising a respective aperture, the apertures of at least two of the pulses differing in number of active transducer elements;
   (c) during (a), activating each transducer element n in the apertures for a total of A(n) times during each of the subsets.

3. The method of claim 1 or 2 wherein the set of pulses transmitted in (a) comprises three pulses having respective relative amplitudes and phases selected from the following non-ordered set:

$i/2-1$, a $i/2$.

4. The method of claim 1 or 2 wherein the set of pulses transmitted in (a) comprises three pulses having respective relative amplitudes and phases selected from the following non-ordered set:

$i/2-1i/2$.

5. The method of claim 1 or 2 wherein the set of pulses transmitted in (a) comprises four pulses having respective relative amplitudes and phases selected from the following non-ordered set:

½, −1, ½.

6. The method of claim 1 or 2 wherein the set of pulses transmitted in (a) comprises four pulses having respective relative amplitudes and phases selected from the following ordered set:

1−½, ½, −1.

7. The method of claim 1 or 2 wherein the set of pulses transmitted in (a) comprises four pulses having respective relative amplitudes and phases selected from the following non-ordered set:

$i/2$, −1, 1, −$i/2$.

8. The method of claim 1 or 2 wherein the set of pulses transmitted in (a) comprises six pulses having respective relative amplitudes and phases selected from the following non-ordered set:

½, −1, ½, ½, −1, ½.

9. The method of claim 1 or 2 wherein the set of pulses transmitted in (a) comprises six pulses having respective relative amplitudes and phases selected from the following non-ordered set:

−½, 1, −½, ½, −1, ½.

10. The method of claim 1 or 2 wherein the set of pulses transmitted in (a) comprises six pulses having respective relative amplitudes and phases selected from the following ordered set:

−½, ½, 1, −1, −½, ½.

11. The method of claim 3 further comprising:
    (d) receiving echo signals from the pulses in the set; and
    (e) combining the echo signals of (d) with respective relative receive weightings selected from the following non-ordered set:

−$i$, 1, $i$.

12. The method of claim 4 further comprising:
    (d) receiving echo signals from the pulses in the set; and
    (e) combining the echo signals of (d) with respective relative receive weightings selected from the following non-ordered set:

$i$, −1, $i$.

13. The method of claim 5 further comprising:
    (d) receiving echo signals from the pulses in the set; and
    (e) combining the echo signals of (d) with respective relative receive weightings selected from the following non-ordered set:

−2, −1, 1, 2.

14. The method of claim 6 further comprising:
    (d) receiving echo signals from the pulses in the set; and
    (e) combining the echo signals of (d) with respective relative receive weightings selected from the following non-ordered set:

1, 2, −2, −1.

15. The method of claim 7 further comprising:
    (d) receiving echo signals of (d) from the pulses in the set; and
    (e) combining the echo signals with respective relative receive weightings selected from the following non-ordered set:

$i2-1$ $1-i2$.

16. The method of claim 8 further comprising:

(d) receiving echo signals of (d) from the pulses in the set; and (e) combining the echo signals with respective relative receive weightings selected from the following non-ordered set:

1, 1, 1, 1, 1, 1.

17. The method of claim 9 further comprising:

(d) receiving echo signals of (d) from the pulses in the set; and (e) combining the echo signals with respective relative receive weightings selected from the following non-ordered set:

1, 1, 1, −1, −1, −1.

18. The method of claim 10 further comprising:

(d) receiving echo signals from the pulses in the set; and (e) combining the echo signals of (d) with respective relative receive weightings selected from the following non-ordered set:

1, −1, 1, −1, 1, −1.

19. The method of claim 1 or 2 wherein all values of A(n), for $0 \leq n < N$, are equal to one another.

20. The method of claim 1 or 2 wherein, for each transducer element n, a single power level P(n) is used for all pulses of each set in which the transducer element n is active.

21. The method of claim 1 or 2 wherein a first subset comprises a first pulse transmitted with N active transducer elements, and wherein a second subset comprises second and third pulses, each transmitted with N/2 active transducer elements, wherein transducer elements that are active in the second pulse are not active in the third pulse, wherein transducer elements that are active in the third pulse are not active in the second pulse, and wherein all of the transducer elements that are active in one of the second and third pulses are active in the first pulse.

22. The method of claim 1 or 2 further comprising:

(d) receiving echo signals from the pulses in the set; and (e) combining the echo signals of (d).

23. The method of claim 22 wherein (e) substantially cancels a fundamental component of the echo signals.

24. The method of claim 1 or 2 wherein all of the pulses of the set are steered along a single acoustic line in (a).

25. The method of claim 1 or 2 wherein at least one of the pulses of the set is steered along a first acoustic line in (a), and wherein at least another one of the pulses of the set is steered along a second acoustic line in (a), spatially distinct from the first acoustic line.

26. The method of claim 1 or 2 wherein each of the apertures comprises active transducer elements distributed across substantially an entire extent of an aperture with a greatest number of active transducer elements of the transducer array.

27. The method of claim 1 or 2 wherein the pulses of the set are characterized by respective amplitudes and phases selected to substantially cancel all transmitted odd-order nonlinearities.

28. The method of claim 1 or 2 wherein at least one of the apertures of (b) comprises a full aperture of the transducer array.

* * * * *